United States Patent [19]
Mackles et al.

[11] Patent Number: 5,407,662
[45] Date of Patent: * Apr. 18, 1995

[54] AQUEOUS MONOPHASIC COMPOSITIONS CONTAINING AROMATIC LIPOPHILES

[76] Inventors: Leonard Mackles, 311 E. 23rd St., New York, N.Y. 10010; Leonard Chavkin, R.R. 1, Box 90, Bloomsbury, N.J. 08804

[*] Notice: The portion of the term of this patent subsequent to Feb. 14, 2006 has been disclaimed.

[21] Appl. No.: 176,067

[22] Filed: Jan. 3, 1994

[51] Int. Cl.$^6$ .......................... A61K 7/16; A61K 7/26
[52] U.S. Cl. ........................................ 424/49; 424/58; 426/651
[58] Field of Search .................................. 424/49–58; 426/651

[56] References Cited
FOREIGN PATENT DOCUMENTS 2190405 2/1974 France .
2552992 4/1985 France .

Primary Examiner—Shep K. Rose
Attorney, Agent, or Firm—Omri M. Behr; Matthew J. McDonald

[57] ABSTRACT

A monophasic colorless transparent liquid aqueous composition comprising 0.05 to 2% by weight of one or more aromatic lipophiles; 0.05 to 2% by weight of the components of a salt of a divalent cation, $M(B)_x$, where M is a divalent cation selected from the group consisting of zinc and magnesium and B is a halide or sulfate and X is 1 when B is sulfate and 2 when B is a halide; 0.05 to 2% by weight of the components of a salt of a monovalent cation, $Na(RSO_4^-)$, where R is selected from the group consisting of $C_8$ to $C_{20}$ alkyl groups; 5–15% by weight ethanol; and water to 100%, provided the ratio of the combined weights of $M(B)_2$ and $Na(RSO_4)_2$ to the weight of said one or more aromatic lipophiles is from 0.8:1 to 2:1, and the stoichiometric ratio of $\{(M^{2+})+(B)_x\}$ to $\{(Na^+)+(RSO_4^-)\}$ is between 3.5:1 and 8:1.

10 Claims, No Drawings

AQUEOUS MONOPHASIC COMPOSITIONS CONTAINING AROMATIC LIPOPHILES

BACKGROUND OF THE INVENTION

This disclosure concerns a novel composition and method for the solubilization of aromatic lipophiles in water.

Aromatic lipophiles are important ingredients in flavoring many aqueous-based products, such as mouthwashes; at levels as low as 0.1% by weight, they are able to impart a fresh pleasing flavor. However, these aromatic oils are difficult to solubilize in aqueous compositions at levels of 0.2% or greater. Given their hydrophobicity, they tend to remain in a phase separate from the aqueous phase, and so detract from the clear, transparent appearance of a monophasic aqueous composition.

Several conventional solutions to this solubilization problem have been proposed. The first of these is the inclusion of co-solvents, most commonly ethyl alcohol. Conventional mouthwashes commonly have to 10 to 30% by weight of ethanol. This high level of co-solvent has been accepted for solubilizing an agent present at only 0.1-1% because ethanol serves several other functions besides solubilizing flavoring agents. For example, it acts as a cleanser, a surface tension lowering agent, a wetting and penetrating agent, and assists antimicrobial activity of any antiseptic ingredients present in the mouthwash.

Despite these multiple beneficial effects, recent epidemiological studies have reported that ethanol in mouthwashes, especially at higher concentrations, has been implicated in causing oral cancer and in poisoning very young children. Therefore, it is now desirable to minimize the amounts of ethanol in mouthwash.

Co-solvent alternatives to ethanol are few in number, especially if the product is one to be ingested. Suitable co-solvents for products to be ingested are limited to glycerine, propylene glycol and other glycols, suitably at levels of 5-30% by weight. As with ethanol, this is a rather high level to effect solubilization of oils present only at 0.2 to 1% by weight. A further drawback is that at levels of 5-30%, glycerine, propylene glycol and other glycols often impart an unpleasant taste to a composition.

Other co-solvents which have conventionally been employed are hydrophilic nonionic surfactants. One such surfactant is a polyethoxylated sorbitan ester (Tweens made by ICI Americas, Inc.). Solubilization of one part of peppermint oil in an aqueous composition requires five (5) parts Tween 80 (polyoxyethylene sorbitan mono oleate). In other words, solubilization of 0.5% of an aromatic oil in water requires at least 2.5% by weight Tweens. At these levels, nonionic surfactants impart an undesirably bitter and soapy flavor to the aqueous composition. A further undesirable effect accompanying this level of nonionic surfactant is the reduction of antimicrobial activity of phenolic preservative, commonly present in mouthwashes.

In order to overcome the problem of the bitter, soapy flavor, a nonionic surfactant which has no taste has been proposed for solubilizing aromatic oils. This surfactant, polyoxyethylene-polyoxypropylene block copolymer (Pluronic 127, made by BASF Corporation) imparts no undesirable taste to the product. However, a substantially higher level of this surfactant is required to solubilize the oil than of Tweens: 1 part of aromatic oil in water requires at least 7 parts of this nonionic to effect solubilization. Although tasteless, these nonionic surfactants are thus not efficient solubilizers. Moreover, they share the undesirable side effect with Tweens of inactivating phenolic germicides such as thymol.

All of the nonionic surfactants conventionally used have a further shortcoming: unlike ethanol, which significantly lowers surface tension, the nonionic surfactants have very little effect on surface tension. In summary, the nonionic surfactant co-solvents do not solubilize as well as ethanol and suffer significant undesirable secondary properties.

Anionic surfactants have also been explored as co-solvents for solubilizing aromatic oils in aqueous compositions. Thus for example, sodium lauryl sulfate has been used alone or in combination with nonionic surfactants as described above. If used at concentrations greater than 0.3% by weight in mouthwashes, anionic surfactants impart a very silky mouth feel to the product. However, anionic surfactants impart a very bitter taste to the aqueous composition and irritate mucous membranes. Further, sodium lauryl sulfate only solubilizes aromatic oils at levels somewhat lower than nonionic surfactants (3 parts sodium lauryl sulfate solubilizes 1 part of a aromatic oil), an aqueous composition containing 0.2% of oil still requires at least 0.6% of sodium lauryl sulfate for solubilization. These strongly undesirable effects render anionic surfactants unsatisfactory as a co-solvent.

In U.S. Pat. No. 4,150,151, problems associated with mouthwash clarity were addressed by including 5-20% ethanol and 0.1-0.6% of a particular alkyl sulfate anionic surfactant mixture along with 0.1-2% of an essential oil as flavorant. The surfactant mixture consisted essentially of dodecyl (or lauryl) and tetradecyl surfactant salts in a weight ratio of 4:1 to 1:1. The cationic moiety could be chosen from, among others, $Na^{1+}$, $K^{1+}$, $Mg^{2+}$ or $NH_4^+$, or mixtures thereof, in a water carrier. The composition optionally further included a nonionic emulsifier, and, if desired, 0-2% of an alkali metal halide. The 4:1 to 1:1 ratio of dodecyl to tetradecyl was said to be critical to keep the composition "water clear," i.e., free of clouding precipitate after storage at or below 35° F. for extended periods of time. Alternatively, for compositions not to be subjected to cold temperatures, the ratio of dodecyl and tetradecyl surfactant salts could be 75:1 to 1:1.

U.S. Pat. No. 4,150,151 does not teach or suggest a desirable ratio of magnesium and halide ions (in equivalent amounts to one another) to be provided in a particular ratio to alkali metal ions with alkyl sulfate ions (again in equivalent amounts to each other). The term "equivalent" as used herein has the standard chemical meaning.

SUMMARY OF THE INVENTION

In a first embodiment, there is provided a composition comprising a monophasic colorless transparent liquid aqueous composition comprising 0.05 to 2% by weight of one or more aromatic lipophiles; 0.05 to 2% by weight of the components of a salt of a divalent cation, $M(B)_x$, where M is a divalent cation selected from the group consisting of zinc and magnesium, B is a halide or sulfate, and x is 1 when B is sulfate and 2 when B is a halide; 0.05 to 2% by weight of the components of a salt of a monovalent cation, $Na(RSO_4)$, where R is selected from the group consisting of $C_8$ to $C_{20}$ alkyl groups; 5 to 15% ethanol by weight; and water to 100%, provided the ratio of the combined weights of the components of $M(B)_2$ and $Na(RSO_4)$ to the weight of said one or more aromatic lipophiles is from 0.8:1 to 2:1, and the stoichiometric ratio of $\{(M^{2+})+(B)_x\}$ to $\{(Na^+)+(RSO_4^-)\}$ is between 3.5:1 and 8:1. It should be noted that the prior art does not suggest or teach such a stoichiometric ratio.

This embodiment has some similarities to one of the embodiments described in Applicants' U.S. patent application Ser. No. 08/177068 (Attorney Reference Code CHAV3.0-020), filed contemporaneously herewith, but differs in the presence of ethanol here. When present at 5 to 15% by weight, ethanol in the present composition improves solubility of the aromatic lipophiles; and when ethanol is present at 10-15% by weight, lower levels of $M(B)_2$ and $Na(RSO_4^-)$ may be used to solubilize the aromatic lipophiles.

In the composition of this embodiment, the weight of the components of $M(B)_x$ may suitably be substantially equal to those of $Na(RSO_4)$. Further, the composition may suitably further comprise 5-25% by weight of a co-solvent selected from the group consisting of glycerine, propylene glycol and polyols.

A second embodiment provides a method of solubilizing one or more aromatic lipophiles in an aqueous suspension to form a monophasic colorless transparent liquid aqueous composition, said method comprising the steps of: combining, in said aqueous suspension, the components of a salt of a monovalent cation, $Na(RSO_4)$, with the components of a salt of a divalent cation, $M(B)_x$, where R is selected from the group consisting of $C_8$ to $C_{20}$ alkyl groups, M is a divalent cation selected from the group consisting of zinc and magnesium, B is a halide or sulfate, and x is 2 when B is a halide and 1 when B is sulfate; and ethanol, such that the ratio of the combined weights of the components of $M(B)_x$ and $Na(RSO_4)$ to the weight of said one or more aromatic lipophiles is from 0.8:1 to 2:1 and the stoichiometric ratio of $\{M^{2+}+(B)_x\}$ to $\{(Na^+)+(RSO_4^-)\}$ is between 3.5:1 and 8:1.

DESCRIPTION OF THE PREFERRED EMBODIMENTS

Applicants have discovered a composition and method for solubilizing aromatic oils in aqueous systems without the drawbacks of conventional systems. The aromatic oil is solubilized in the aqueous composition by a combination of 5-10% by weight ethanol with 0.05 to 2% by weight of the components of a salt of a divalent cation, $M(B)_x$ and 0.05 to 2% by weight of the components of a salt of a mono-valent cation, $Na(RSO_4^-)$, where M is a divalent cation selected from the group consisting of zinc and magnesium, and B is a halide or sulfate and x is 1 when B is sulfate and 2 when B is a halide; and R is selected from the group consisting of $C_8$ to $C_{20}$ alkyl groups. The composition is monophasic and transparent, but has no unpleasant taste and does not irritate mucous membrane.

In a first embodiment, there is provided a composition comprising a monophasic colorless transparent liquid aqueous composition comprising 0.05 to 2% by weight of one or more aromatic lipophiles; 0.05 to 2% by weight of the components of a salt of a divalent cation, $M(B)_x$, where M is a divalent cation selected from the group consisting of zinc and magnesium, B is a halide or sulfate, and x is 1 when B is sulfate and 2 when B is a halide; 0.05 to 2% by weight of the components of a salt of a monovalent cation, $Na(RSO_4)$, where R is selected from the group consisting of $C_8$ to $C_{20}$ alkyl groups; 5 to 15% by weight ethanol, and water to 100%, provided the ratio of the combined weights of the components of $M(B)_2$ and $Na(RSO_4)$ to the weight of said one or more aromatic lipophiles is from 0.8:1 to 2:1, and the stoichiometric ratio of $\{(M^{2+})+(B)_x\}$ to $\{(Na^+)+(RSO_4^-)\}$ is between 3.5:1 and 8:1.

In Applicants' U.S. patent application Ser. No. 08/177068 (Attorney Reference Code CHAV3.0-020), $M(RSO_4^-)_2$ alone may be added to an ethanol-free aqueous composition to solubilize aromatic lipophiles. In the present invention, two salts are added to an aqueous composition to solubilize aromatic oils in place of $M(RSO_4^-)_2$ alone. These two salts, a divalent cation salt $M(B)_x$ and a monovalent cation salt $NaRSO_4$, are slightly more available from commercial sources.

The composition of this first embodiment solubilizes one or more aromatic oils in an aqueous composition with $M(B)_x$ and $Na(RSO_4)$ salts, in which the weight ratio of $M(B)_x$ and $Na(RSO_4)$ to the oil(s) is from 0.8:1 to 2:1. Since the $Mg(B)_x$ and the $Na(RSO_4)$ will be partially dissociated in the aqueous composition, the weight ratio is more accurately expressed as a ratio between the combined weights of the components of $Mg(B)_x$ and $Na(RSO_4)$ to the weight of the one or more aromatic oil. This ratio has a value of from 0.8:1.

Suitably the R group may be predominantly a $C_{12}$ alkyl, making $RSO_4^-$ a lauryl sulfate group. Further, M may be magnesium.

Aromatic lipophiles which are suitable for solubilization in this composition include peppermint oil, thymol, menthol, eucalyptol and methyl salicylate.

It is noted that the composition may further incorporate from 5-25% by weight of a co-solvent. Suitable co-solvents include glycerine, propylene glycol and polyols. The presence of one or more of said co-solvents may lower the amount of divalent cation salt components required for solubilization of the aromatic lipophile. Accordingly, when said co-solvent is present, generally the ratio of the combined weights of the components of the divalent cation salt to the weight of said one or more aromatic lipophiles may be at from approximately 1:1 to 1.5:1.

The ratio of the combined weights of the components of the salts $M(B)_x$ and $NaRSO_4)_2$ to the weight of the one or more aromatic lipophiles is an important aspect of this invention. If this ratio between the weights of the salt components and the aromatic lipophiles is less than 0.8:1, then solubilization is incomplete and the composition is not monophasic, colorless or transparent. By contrast, if the ratio is greater than 2:1, a monophasic transparent liquid is obtained; but the presence of the divalent cation salt components begins to become noticeable in the taste of the composition. Therefore, the maximum level desirable of said divalent cation salt components in the composition is two times the weight of the aromatic lipophile.

The composition of this embodiment is a monophasic composition when two conditions are met. The first of these is that the ratio of the combined weights of the two salts' components to the aromatic oils is from 0.8:1 to 2:1. This ratio is distinguished from that in U.S. patent application Ser. No. 08/177068, (Attorney Reference Code CHAV3.0-020) in that less of the salt components is required for solubilization. It is not clear why the lower endpoint of the ratio range may be lower than when $M(RSO_4)_2$ is added directly in U.S. patent application Ser. No. 08/177068 (Attorney Reference Code CHAV3.0-020); just as in that application, the two salts here dissociate to some degree into their ionic components once added to water. However, the salt components of the present invention may reassociate to some degree either as the original salts or as variants thereof, e.g., $M(RSO_4)_2$ and NaB. The present invention therefore appears to produce the $M(RSO_4)_2$ of the first embodiment in situ. Without in any way limiting the invention, it is Applicants' belief that this formation of magnesium lauryl sulfate in situ, combined with what is believed to be a "salting in" effect by both the monovalent and divalent salt components, is responsible for solubilizing the aromatic oil. In fact, these phenomena are believed to solubilize the aromatic oils even when the ratio of the salt components to that of the aromatic oil is lower than the 1:1 minimum ratio value in U.S. patent application Ser. No. 08/177068 (Attorney Reference Code CHAV3.0-020). Whether or not these phenomena do permit the solubilization at the lower ratio value, it is clear that the level of salt components' weight to the of the aromatic oil may be reduced in this second embodiment to a minimum level of 0.8:1.

The second condition needed for solubilization is that the stoichiometric ratio of the components of the two original salts $\{M^{2+}+B\}$ to $\{Na+RSO_4\}$—i.e., the ratio of equivalents of $\{M^{2+}+B\}$ to $\{Na+RSO_4\}$—be from 3.5:1 to 8:1. This stoichiometric ratio is based on the equation (when $M^{2+}$ is magnesium and B is Cl):

$$MgCl_2 + 2NaRSO_4 > Mg(RSO_4^-)_2 + 2NaCl.$$

It is surprising that the stoichiometric ratio range needed for solubilization should be as high as 3.5:1 to 8:1. In the aforementioned U.S. patent application Ser. No. 08/177068 (Attorney Reference Code CHAV3.0-020), it is the weight ratio between $M(RSO_4^-)_2$ and the aromatic oil which makes the composition stable as a monophase. Thus, it might seem that to replace the $M(RSO_4^-)_2$ of this contemporaneously filed application with the two salts $M(B)_x$ and $NaRSO_4$ of the present invention, one would attempt to convert as much of the M cation in the $M(B)_x$ salt to $M(RSO_4^-)_2$ in the final composition as possible. One might be led to do this by adding at least two moles of $NaRSO_4$ for each mole $M(B)_x$, so that each $M^{2+}$ cation would always have at least two $RSO_4^-$ anions with which to pair. In other words, one would attempt to maintain the stoichiometric ratio at a value of 1:1 or less.

However, it is unexpectedly found that the stoichiometric ratio range of $\{(M^{2+})+(B)_x\}$ to $\{(Na^+)+(RSO_4^-)\}$ which maintains the composition as a monophase is not a ratio of 1:1 or lower, corresponding to the molar ratio of $1M^{2+}:2(RSO_4^-)$ in $M(RSO_4)_2$. On the contrary, in order to maintain the composition in a monophase, there must 3.5 to 8 equivalents of $M(B)_x$ for each equivalent of $NaRSO_4$. It would appear that this ratio provides $M^{2+}$ cations in excess over the $RSO_4^-$ anions. Thus, at a stoichiometric ratio of 3.5:1, there are provided 3.5 equivalents (or 1.75 moles) of $M^{2+}$ and 1 equivalent (or 1 mole) of $RSO_4^-$, leaving an apparent excess of 2.5 equivalents (or 1.25 moles) of $M^{2+}$; and at a ratio of 8:1, there are provided 8 equivalents (or 4 moles) of $M^{2+}$ to 1 equivalent (or 1 mole) of $RSO_4^-$, leaving an apparent excess of 7 equivalents (or 3.5 moles) of $M^{2+}$.

Solubilization of the aromatic lipophiles is improved in this embodiment by the inclusion of ethanol at 5 to 15% by weight of the composition. When ethanol is present at levels of 10% up to 15% by weight, then lower levels of $M(B)_x$ and $Na(RSO_4^-)$ may be used to solubilize the aromatic lipophiles. Thus, in a composition containing from 0 to about 9% by weight ethanol, 0.15% by weight of both of $M(B)_x$ and $Na(RSO_4^-)$ solubilize aromatic oils; whereas, when ethanol is present at 10%, only 0.10% by weight of both of these salts solubilize the aromatic oils.

In a second embodiment of the invention, there is provided a method of solubilizing one or more aromatic lipophiles in an aqueous suspension. This embodiment comprises the steps of: combining, in said aqueous suspension, the components of a salt of a monovalent cation, $Na(RSO_4)$, with the components of a salt of a divalent cation, $M(B)_x$, where R is selected from the group consisting of $C_8$ to $C_{20}$ alkyl groups, M is a divalent cation selected from the group consisting of zinc and magnesium, B is a halide or sulfate, and x is 2 when B is a halide and 1 when B is sulfate, provided that the ratio of the combined weights of the components of $M2(B)_x$ and $Na(RSO_4)$ to the weight of said one or more aromatic lipophiles is from 0.8:1 to 2:1 and the stoichiometric ratio of $\{(M^{2+})+(B)_x\}$ to $\{(Na^+)+(RSO_4^-)\}$ is between 3.5:1 and 8:1. The ingredients of the aqueous composition may be added in this method in any order, i.e., the aromatic lipophile need not be introduced into the water prior to the addition of the $M(RSO_4)_2$.

While the present invention has been explained in relation to its preferred embodiments, it is to be understood that variations thereof will be apparent to those skilled in the art upon reading this specification. Thus, the present invention is intended to cover all variations which fall within the scope of the appended claims.

EXAMPLE I 0.20 grams of natural peppermint oil was mixed with varying amounts of Tween 80 surfactant (polysorbate 80 from ICI Corp., a mixture of oleate esters of sorbitol and sorbitol anhydride consisting predominantly of the monoester condensed with 20 moles ethylene oxide) in a sufficient amount of water to give a total of 100 grams. The mixture was stirred until a clear solution was obtained. 1.00 gram of Tween 80 were required to effect solution at 15° C.

EXAMPLE II 0.20 grams of natural peppermint oil was mixed with varying amounts of Pluronic 127 surfactant from BASF Corp., polyoxyethylene-polyoxypropylene block copolymer, conforming generally to the formula:

$$HO(CH_2CH_2O)_X(CHCH_2O)_Y(CH_2CH_2O)_ZH$$
$$CH_3$$

(in which the average values of X, Y and Z are 98, 67 and 98), and a sufficient amount of water to give a total of 100 grams. The mixture was stirred until a clear solution was obtained. 1.40 grams of Pluronic 127 were required to effect solution at 25° C.

EXAMPLE III 0.20 grams of natural peppermint oil was mixed with varying amounts of sodium lauryl sulfate surfactant (USP Texapon LS 100 F from Henkel Corp.) in a sufficient amount of water to give a total of 100 grams. The mixture was stirred until a clear solution was obtained.

0.60 grams of sodium lauryl sulfate were required to effect solution at 25° C.

EXAMPLE IV 0.20 grams of natural peppermint oil was mixed with varying amounts of magnesium lauryl sulfate (ELFAN 240 from Akzo Corp.) in a sufficient amount of water to give a total of 100 grams. The mixture was stirred until a clear solution was obtained. 0.20 grams of magnesium lauryl sulfate were required to effect solution at 25° C.

EXAMPLE V 0.20 grams of natural peppermint oil was mixed with varying amounts of sodium lauryl sulfate (USP Texapon LS 100 F from Henkel Corp.), an equal weight of anhydrous magnesium sulfate, 5 grams of ethanol and a sufficient amount of water to give a total of 100 grams. The mixture was stirred until a clear solution was obtained. 0.15% Sodium lauryl sulfate and magnesium sulfate were required to effect solutions at 25° C.

EXAMPLE VI 0.20 grams of natural peppermint oil was mixed with varying amounts of sodium lauryl sulfate and an equal amount of zinc chloride, 5 grams of ethano, and a sufficient amount of water to give a total of 100 grams. The mixture was stirred until a clear solution was obtained. 0.10% of sodium lauryl sulfate and zinc chloride were required to effect solution at 25° C.

| | Ex. I | Ex. II | Ex. III | Ex. IV | Ex. V | Ex. VI |
|---|---|---|---|---|---|---|
| Tween 80 | 1.0 g | | | | | |
| Pluronic 127 | | 1.4 g | | | | |
| Sodium Lauryl Sulfate | | | 0.6 g | | | |
| Magnesium Lauryl Sulfate | | | | 0.2 g | | |
| Sodium Lauryl Sulfate | | | | | 0.15 g | |
| Magnesium Sulfate | | | | | 0.15 g | |
| Ethanol | | | | | 5.0 g | |
| Sodium Lauryl Sulfate | | | | | | 0.10 g |
| Zinc Chloride | | | | | | 0.10 g |
| Ethanol | | | | | | 5.0 g |

It can be seen from the above that the material needed to solubilize the peppermint oil is reduced significantly. The solubilizers of Examples V and VI are 3–5 times more effective than the conventional solubilizers of the prior art represented by the compositions of Examples I through III.

Repeating Examples V and VI with a higher level of ethanol demonstrates that the level of monovalent and bivalent salts may be lowered when the level of ethanol rises: solubilization occurs at only 0.10 gram of magnesium sulfate and sodium lauryl sulfate in Example VII, and with only 0.075 in Example VIII, in contrast to 0.15 and 0.10 gram of each in Examples V and VI respectively.

| | Ex. VII | Ex. VIII |
|---|---|---|
| Magnesium Sulfate | 0.10 g | |
| Sodium Lauryl Sulfate | 0.10 g | |
| Ethanol | 10 g | |
| Zinc Chloride | | .075 g |
| Sodium Lauryl Sulfate | | .075 g |
| Ethanol | | 10 g |

EXAMPLE IX

The following essential oil mixture was used to formulate a mouthwash:

| | |
|---|---|
| Menthol | 16.0% |
| Eucalyptol | 36.0 |
| Methyl Salicylate | 24.0 |
| Thymol | 24.0 |
| Total | 100.0% |

0.50 gram of this mixture is combined 10.0 grams ethanol, 0.25 grams of sodium lauryl sulfate, and 0.25 grams magnesium sulfate, 5 grams propylene glycol and sufficient amount of water to give 100 grams. This solubilizes the essential oil. The ratio of the combined salt components to that of the oil was 0.5:0.5. Similarly, 1 gram of essential oil is solubilized by 0.45 grams sodium lauryl sulfate and 0.45 grams magnesium sulfate, as is 2 grams oil mixture by 0.9 grams sodium lauryl sulfate and 0.9 grams magnesium sulfate.

We claim:

1. A monophasic colorless transparent liquid aqueous composition comprising
   a) 0.05 to 2% by weight of one or more aromatic lipophiles;
   b) 0.05 to 2% by weight of the components of a salt of a divalent cation, $M(B)_x$, where M is a divalent cation selected from the group consisting of zinc and magnesium; and B is a halide or sulfate and x is 1 when B is sulfate and 2 when B is a halide;
   c) 0.05 to 2% by weight of the components of a salt of a monovalent cation, $Na(RSO_4^-)$, where R is selected from the group consisting of $C_8$ to $C_{20}$ alkyl groups;
   d) 5 to 15% by weight of ethanol; and
   e) water to 100%, provided the ratio of the combined weights of the components of $M(B)_2$ and $Na(RSO_4^-)$ to the weight of said one or more aromatic lipophiles is from 0.8:1 to 2:1, and the stoichiometric ratio of $\{(M^{2+})+(B)_x\}$ to $\{(Na^+)+(RSO_4^-)\}$ is between 3.5:1 and 8:1.

2. The composition according to claim 1 wherein said R is predominantly a $C_{12}$ alkyl.

3. The composition according to claim 1 wherein $RSO_4^-$ is lauryl sulfate.

4. The composition according to claim 3 wherein M is magnesium.

5. The composition according to claim 1 comprising 10 to 15% by weight of ethanol.

6. The composition according to claim 1 wherein said one or more aromatic lipophiles are selected from the group consisting of oil of peppermint, thymol, menthol, eucalyptol and methyl salicylate.

7. The composition according to claim 1 further comprising 5–25% by weight of a co-solvent selected from the group consisting of glycerine, propylene glycol and polyols.

8. The composition according to claim 1 wherein the weight of the components of $M(B)_x$ is substantially equal to the weight of the components of $Na(RSO_4)$.

9. The composition according to claim 1 where M is magnesium and B is chloride or sulfate.

10. A method of solubilizing one or more aromatic lipophiles in an aqueous suspension to form a monophasic colorless transparent composition, comprising combining, in said aqueous suspension, the components of a salt of a monovalent cation, Na(RSO$_4^-$), with the components of a salt of a divalent cation, M(B)$_x$, where R is selected from the group consisting of C$_8$ to C$_{20}$ alkyl groups;

M is a divalent cation selected from the group consisting of zinc and magnesium; B is a halide or sulfate; and x is 1 when B is sulfate and 2 when B is a halide, provided that the ratio of the combined weights of the components of M(B)$_x$ and Na(RSO$_4$) to the weight of said one or more aromatic lipophiles is from 0.8:1 to 2:1, and the stoichiometric ratio of $\{(M^{2+})+(B)_x\}$ to $\{(Na^+)+(RSO_4^-)\}$ is between 3.5:1 and 8:1.

* * * * *